(12) United States Patent
Grueebler (10) Patent No.: US 11,224,539 B2
(45) Date of Patent: Jan. 18, 2022

(54) COATED FORCEPS FOR IMPROVED GRASPING

(71) Applicant: Novartis AG, Basel (CH)

(72) Inventor: Reto Grueebler, Greifensee (CH)

(73) Assignee: Alcon Inc., Fribourg (CH)

(*) Notice: Subject to any disclaimer, the term of this patent is extended or adjusted under 35 U.S.C. 154(b) by 753 days.

(21) Appl. No.: 16/006,506

(22) Filed: Jun. 12, 2018

(65) Prior Publication Data

US 2019/0000670 A1 Jan. 3, 2019

Related U.S. Application Data

(60) Provisional application No. 62/525,983, filed on Jun. 28, 2017.

(51) Int. Cl.
| | | |
|---|---|---|
| *A61B 17/29* | (2006.01) | |
| *A61F 9/007* | (2006.01) | |
| *A61B 17/30* | (2006.01) | |
| *A61B 17/00* | (2006.01) | |

(52) U.S. Cl.
CPC .......... *A61F 9/00736* (2013.01); *A61B 17/29* (2013.01); *A61B 17/30* (2013.01); *A61B 2017/00858* (2013.01); *A61B 2017/00942* (2013.01); *A61B 2017/00955* (2013.01); *A61B 2017/2926* (2013.01); *A61B 2017/305* (2013.01)

(58) Field of Classification Search
CPC ..... A61F 9/00736; A61B 17/29; A61B 17/30; A61B 2017/00858; A61B 2017/00942; A61B 2017/00955; A61B 2017/2926; A61B 2017/305; A61B 2017/301; A61B 2017/303; A61B 17/28; A61B 17/50
See application file for complete search history.

(56) References Cited

U.S. PATENT DOCUMENTS

| | | |
|---|---|---|
| 5,921,998 A | 7/1999 | Tano |
| 8,945,125 B2 | 2/2015 | Schechter |
| 10,004,525 B2 | 6/2018 | Scheller |
| (Continued) | | |

FOREIGN PATENT DOCUMENTS

| | | |
|---|---|---|
| GB | 2086792 A | 5/1982 |
| WO | 2014092956 A1 | 6/2014 |
| WO | 2015124467 A1 | 8/2015 |

OTHER PUBLICATIONS

Valentin-Rodriguez, et al.; Tuning the adhesion of layer-by-layer films to the physicochemical properties of inner imiting membranes using nanoparticles; Micron; vol. 42; pp. 616-624 (2011).
(Continued)

*Primary Examiner* — Erich G Herbermann (57) ABSTRACT

Surgical instruments for use in membrane peeling in treatments of different macular surface diseases are disclosed herein. Membrane forceps may include a forceps extension and forceps jaws extending from a distal termination of the forceps extension. The forceps jaws may include a first jaw and a second jaw. Each of the first jaw and the second jaw may include a gripping tip that abuts one another when the forceps jaws are in a closed configuration so as to grasp a membrane The first jaw and the second jaw may each include a coating at a distal end of the forceps jaws configured to increase a frictional force between the membrane and the forceps jaws.

15 Claims, 10 Drawing Sheets

(56) References Cited

U.S. PATENT DOCUMENTS

| | | |
|---|---|---|
| 10,039,565 B2 | 8/2018 | Vezzu |
| 10,588,652 B2 | 3/2020 | Scheller |
| 2007/0239202 A1 | 10/2007 | Rodriguez |
| 2011/0015669 A1 | 1/2011 | Corcosteugi |
| 2014/0005653 A1* | 1/2014 | Shelton, IV ............ A61B 34/70 606/33 |
| 2014/0135820 A1 | 5/2014 | Schaller |
| 2014/0276407 A1* | 9/2014 | DeVries .............. A61J 15/0015 604/103.08 |
| 2014/0277110 A1* | 9/2014 | Scheller ................. A61B 17/30 606/207 |
| 2015/0088193 A1 | 3/2015 | Scheller |
| 2015/0164534 A1 | 6/2015 | Felder |
| 2015/0238355 A1* | 8/2015 | Vezzu .................... A61B 17/30 606/207 |
| 2016/0296246 A1 | 10/2016 | Schaller |
| 2017/0056038 A1 | 3/2017 | Hess |
| 2018/0103972 A1 | 4/2018 | Grueebler |
| 2018/0368911 A1 | 12/2018 | Van Overdam |

OTHER PUBLICATIONS

Valentin-Rodriguez, C., Tezel, T. H., & Ivanisevic, A.; Surface modification of vitreoretinal surgical instruments with layer-by-layer films; Wiley Periodicals, Inc.; vol. 33; pp. 1-5 (2011).

Valentin-Rodriguez, et al.; "Quantitative analysis of human internal limiting membrane extracted from patients with macular holes"; Langmuir; vol. 26; No. 15; pp. 12810-12816; (2010).

Huber, et al.; "Evidence for capillarity contributions to gecko adhesion from signle spatula nanomechanical measurements"; PNAS; vol. 102; No. 34: pp. 16293-16296; Nov. 8, 2005.

Greiner, et al.; Adhesion of bioinspired micropatterned surfaces: Effects of pillar readius, aspect ratio, and preload Langmuir; vol. 23; pp. 3495-3502; (2007).

Arzt, Eduard, et al. "From micro to nano contacts in biological attachment devices"; PNAS, vol. 100; No. 19; pp. 10603-10606; Sep. 16, 2003.

Gillies, et al.; Shear adhesion strength of thermoplastic gecko-inspired synthetic adhesive exceeds material limits Langmuir; vol. 27; pp. 11278-11281; (2011).

Fischer, et al.; "Bioinspired polydimethylsiloxane-based composites with high shear rsistance against wet tissue"; Journal of the Mechanical Behavior of Biomedical Materials; pp. 87-95; (2016).

Mahdavi, A., et al.; "A biodegradable and biocompatible gecko-inspired tissue adhesive"; PNAS; vol. 105; No. 7; pp. 2307-2312; Feb. 19, 2008.

Paretkar, Dadhichi, et al. "Preload-responsive adhesion: effects of aspect ratio, tip shape and alignment"; Journal of the Royal Society Interface; vol. 10; pp. 1-13; 20130171. http://dx/doi.org/10.1098/rsif.2013.0171.

Barreu, et al.; "Fibrillar elastomeric micropatterns create tunable adhesion even to rough surfaces"; Adv. Funct. Mater.; vol. 26; pp. 4687-4694; (2016).

\* cited by examiner

COATED FORCEPS FOR IMPROVED GRASPING

CROSS-REFERENCE TO RELATED APPLICATIONS

This application claims the benefit of U.S. Provisional Application No. 62/525,983, filed Jun. 28, 2017, the entire contents of which are incorporated herein by reference.

BACKGROUND

Internal limiting membrane (ILM) peeling and epi-retinal membrane (ERM) peeling are useful surgical treatments of different macular surface diseases, such as macular hole vitreo-macular traction syndrome, macular pucker, diabetic macular edema, and cystoid macular edema secondary to inflammatory or venous occlusive diseases. However, the surgical techniques for ILM and ERM peeling typically require skill and patience. Instruments used for each segment of the surgical technique may be precise and carefully constructed surgical instruments to ensure a successful procedure.

The surgical treatment itself includes grasping an edge of the membrane, and peeling the membrane. One technique for membrane peeling may be a two-step procedure. First, an edge may be created on the membrane for the surgeon to grasp. By way of example, some surgeons use a scraper to gain the edge. Next, the surgeon may use a special membrane forceps to grasp and peel the membrane from the surface of the retina. However, current techniques may require application of a normal force into the retina to provide sufficient friction for the membrane forceps to grasp the membrane. This normal force may lead to inadvertent damage of underlying retinal cells.

SUMMARY

In an exemplary aspect, the present disclosure is directed to an ophthalmic membrane forceps that may include a forceps extension and forceps jaws extending from a distal termination of the forceps extension. The forceps jaws may include a first jaw including a first gripping tip, a second jaw including a second gripping tip, and a coating disposed on a distal end of the forceps jaws. The coating may be configured to increase a coefficient of friction with an ophthalmic membrane. The first gripping tip and the second gripping tip may abut one another when the forceps jaws are in a closed configuration.

In another exemplary aspect, the present disclosure is directed to an ophthalmic surgical instrument. The ophthalmic surgical instrument may include a membrane forceps and an actuation tube. The membrane forceps may include a forceps extension and forceps jaws extending from a distal termination of the forceps extension. The forceps jaws may include a first jaw including a first gripping tip, a second jaw including a second gripping tip, and a coating formed on a distal end of each of the first jaw and the second jaw. The coating may be configured to increase a coefficient of friction with an ophthalmic membrane. The first gripping tip and the second gripping tip may be configured to abut one another when the forceps jaws are in a closed configuration.

In another exemplary aspect, the present disclosure is directed to a method for peeling an ophthalmic membrane. The method may include inserting a membrane forceps into an eye of a patient, advancing the membrane forceps to a membrane on a retina in the eye, and closing the membrane forceps such that the membrane is grasped between gripping tips at a distal end of the membrane forceps. A coating at the distal end may increase a frictional force between the membrane and the gripping tips as the membrane forceps are closed.

The different aspects may include one or more of the following features. The coating may be disposed on at least a portion of a leading surface of each of the first jaw and the second jaw. The leading surface may not include the gripping tips. The coating may include a charged coating. The charged coating may include at least one coating selected from the group consisting of a positively charged, hydrophilic amine coating; a negatively charged, sulfonate coating; a multilayer polyelectrolyte coating; and a negatively charged hydroxyl coating. The coating may include a polydimethyl siloxane coating. The coating may include a textured coating. The textured coating may include a pillar coating or a suction-cup coating. A surface of the forceps jaws covered by the coating may exclude the first gripping tip and the second gripping tip. The coating may be disposed on a leading surface of each of the first jaw and the second jaw, the leading surface terminating at the corresponding first gripping tip and second gripping tip. The first jaw and the second jaw may each be arcuate in shape. The first jaw and the second jaw each may include a first bend and a second bend. The second bend in each of the first jaw and the second jaw may cause the distal end of the membrane forceps to curve toward a longitudinal axis of the membrane forceps. The leading surface of each of the first jaw and the second jaw may extend from the second bend to the corresponding gripping tip. The ophthalmic surgical instrument may further include a handle and a tube actuation assembly coupled to the handle and the actuation tube. The tube actuation assembly may be operable to close the forceps jaws by causing the actuation tube to move over the forceps jaws It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate implementations disclosed herein and together with the description, serve to explain the principles of the present disclosure.

DETAILED DESCRIPTION

For the purposes of promoting an understanding of the principles of the present disclosure, reference will now be made to the implementations illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

The present disclosure generally relates to surgical instruments for use in membrane peeling in treatments of different macular surface diseases. In accordance with example embodiments disclosed herein, membrane forceps are provided that include a coating to allow gripping of the membrane with a reduced force into the retina. With the reduced indentation force, damage to the retina from the membrane forceps may be reduced. The reduced indentation force may be achieved by coating the leading surface of the membrane forceps with a material that increases the coefficient of friction between the membrane and the membrane forceps. In addition, coating the leading surface may also better enable a surgeon to form an edge on the membrane, which can then be grasped.

Figure 1:
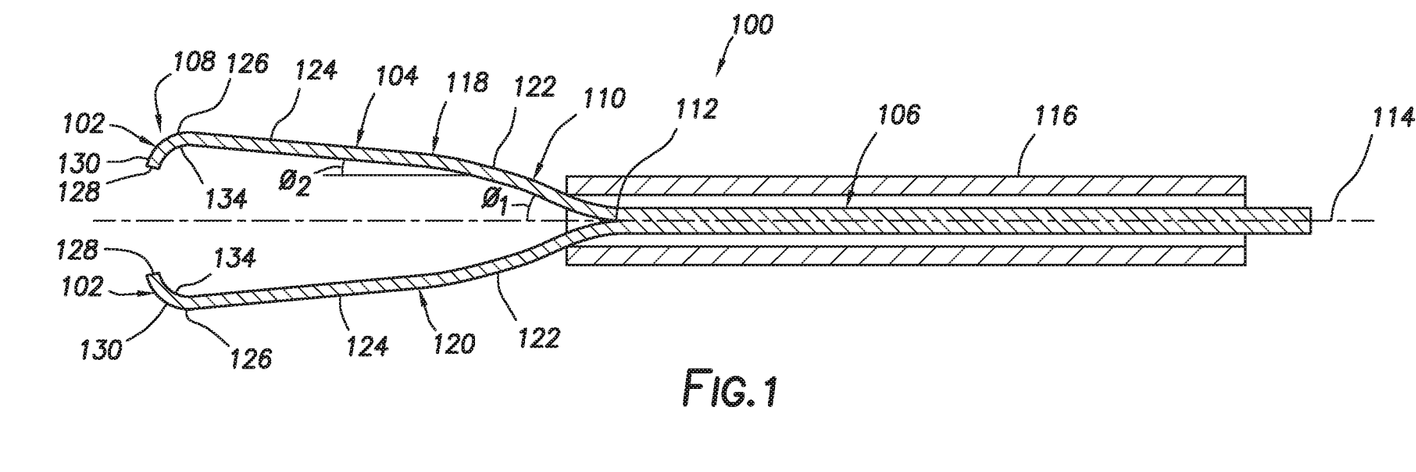
FIG. 1 illustrates a cross-sectional view of an example membrane forceps in an open configuration.
Figure 2:
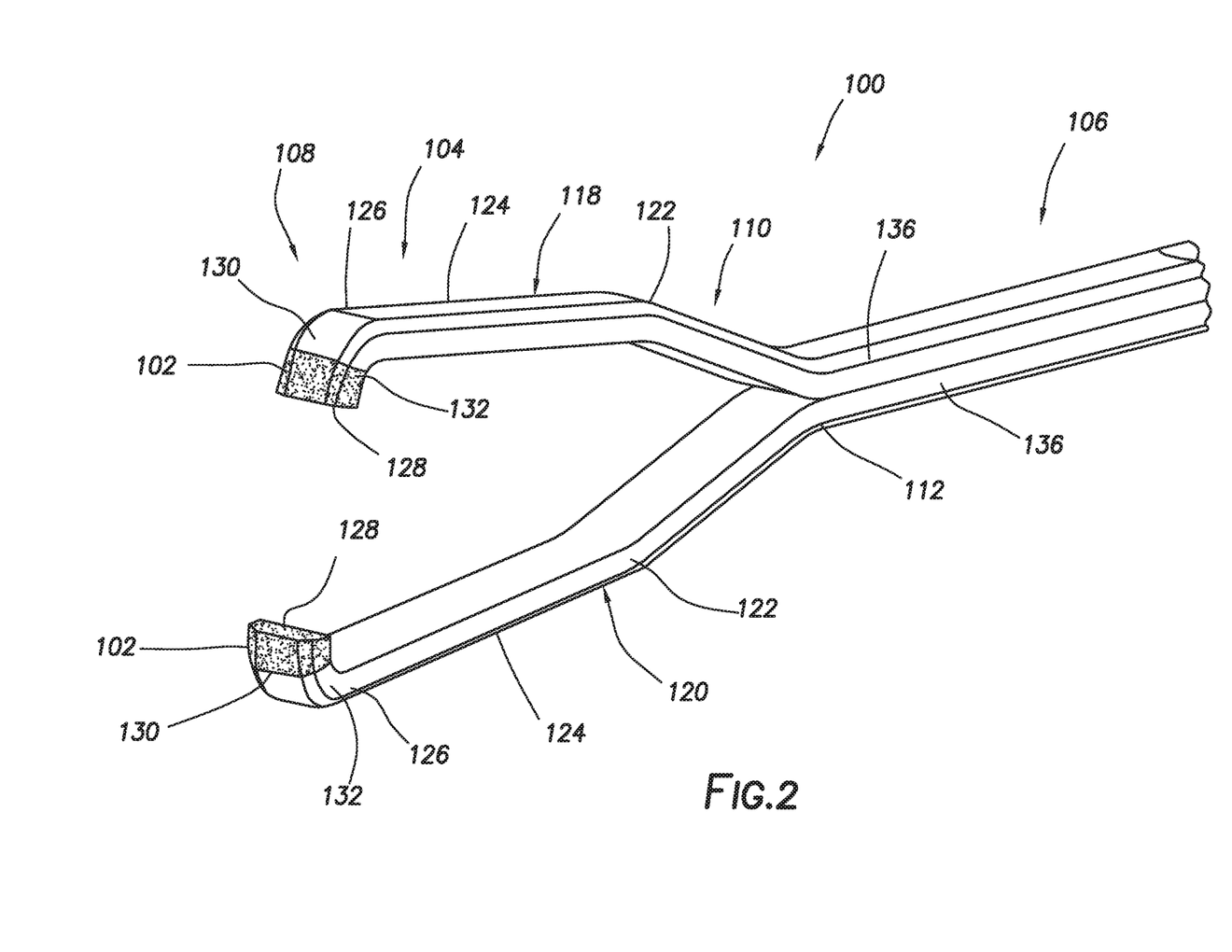
FIG. 2 illustrates a perspective view of an example membrane forceps in an open configuration.

FIGS. 1 and 2 illustrate an example membrane forceps 100 that includes a coating 102. As illustrated, the membrane forceps 100 may include forceps jaws 104 and a forceps extension 106. The coating 102 may be at a distal end 108 of the forceps jaws 104. At a proximal end 110, the forceps jaws 104 may extend from a distal termination 112 of the forceps extension 106. The forceps jaws 104 and the forceps extension 106 may extend along a longitudinal axis 114, which may be defined by an actuation tube 116. For clarity, the actuation tube 116 is omitted in the cross-sectional view of FIG. 2. The forceps jaws 104 and the forceps extension 106 may be made from any suitable material, including, but not limited, to a metal or thermoplastic, among others.

The forceps jaws 104 may include a first jaw 118 and a second jaw 120. While the forceps jaws 104 may extend along the longitudinal axis 114, each of the first jaw 118 and the second jaw 120 may extend from the distal termination 112 of the forceps extension 106 at a first angle $\theta_1$ relative to the longitudinal axis 114. The first angle $\theta_1$ may range from about 5° to about 45°. The first jaw 118 and the second jaw 120 may each be arcuate in shape. For example, the first jaw 118 and the second jaw 120 may each include a first bend 122. The first bend 122 in the first jaw 118 and the second jaw 120 may reduce the angle of deflection of the forceps jaws 104 such that a middle portion 124 of the first jaw 118 and the second jaw 120 has a second angle $\theta_2$ with respect to the longitudinal axis 114 that is less than the first angle $\theta_1$. For example, the second angle $\theta_2$ may be about 10% to about 75% less than the first angle $\theta_1$. For example, the second angle $\theta_2$ may range from about 2° to about 30°. However, angles outside of the disclosed ranges for the first angle $\theta_1$ and the second angle $\theta_2$ are also contemplated. The first jaw 118 and the second jaw 120 may also each include a second bend 126 that is longitudinally spaced from the first bend 122. As illustrated, the second bend 126 may be at the distal end 108 of the forceps jaws 104. The second bend 126 may be curved, for example, to cause the distal end 108 to curve toward the longitudinal axis 114.

At the distal end 108, the first jaw 118 and the second jaw 120 may each include a gripping tip 128. As illustrated, the first jaw 118 and the second jaw 120 each terminate at the corresponding gripping tip 128. The second bend 126 in the forceps jaws 104 may be sufficient to cause the gripping tips 128 to curve toward the longitudinal axis 114. In this manner, closing of the forceps jaws 104 should move the gripping tips 128 together to abut one another so that material (e.g., membrane 1010 shown in FIGS. 10-12 and 14) may be gripped between the gripping tips 128.

At the distal end 108, the first jaw 118 and the second jaw 120 may also each include a leading surface 130. When in use, the leading surface 130 may engage material (e.g., membrane 1010 shown in FIGS. 10-12 and 14) as the gripping tips 128 may be used to grasp the material. In some embodiments, the leading surface 130 may be at least substantially planar, i.e., planar or within 5° or less of planar. The leading surface 130 may extend from the second bend 126 and terminate at the gripping tip 128. At the respective distal ends 108, each of the first jaw 118 and the second jaw 120 may also include a trailing surface 134 and lateral surfaces 132 (as shown in FIG. 2) that connect the trailing surface 134 and the leading surface 130. The trailing surface 134 may be opposed to the leading surface 130.

The coating 102 may be disposed on the leading surface 130. As best seen on FIG. 2, the coating 102 may also be disposed on lateral surfaces 132. By application of the coating 102, the coefficient of friction between the forceps jaws 104 and the material (e.g., membrane 1010 shown in FIGS. 10-12 and 14) may be increased such that less indentation force may be needed for the gripping tips 128 to grasp the material. As a result of the increased friction and decreased indentation, there is a reduced risk of incarcerating the retinal sensory tissues while removing the inner limiting membrane (ILM), for example. In the illustrated embodiment, the coating 102 does not completely coat the leading surface 130 and/or lateral surfaces 132. Instead, the coating 120 partially coats the leading surface 130 and/or lateral surfaces 132. For example, the coating 102 may be disposed on from about 10% to about 100% of the leading surface 130 and/or on from about 10% to about 100% of the lateral surfaces 132. Any suitable technique may be used for application of the coating 102 onto the distal end 108. FIG. 2 also shows the gripping tips 128 having the coating 102. In other implementations, the gripping tips 128 may be free of the coating 102. Examples of coating techniques that may be used to apply the coating 102 include, but are not limited to, spray coating, vapor deposition, dip coating, and spin coating, among others. In some embodiments, the coating 102 may be applied with an adhesive (not shown).

The forceps extension 106 may extend longitudinally from the forceps jaws 104. As illustrated on FIG. 2, the forceps extension 106 may include extensions 136 of each of the first jaw 118 and the second jaw 120. In some instances, the extensions 136 may be attached at one or more locations along the lengths thereof. For example, in some instances, the extensions 136 may be joined by one or more welds. Alternatively, the forceps extension 106 may be a unitary member (not shown) from which the forceps jaws 104 extend. As illustrated on FIG. 1, the forceps extension 106 may be at least partially disposed in the actuation tube 116.

Figure 3:
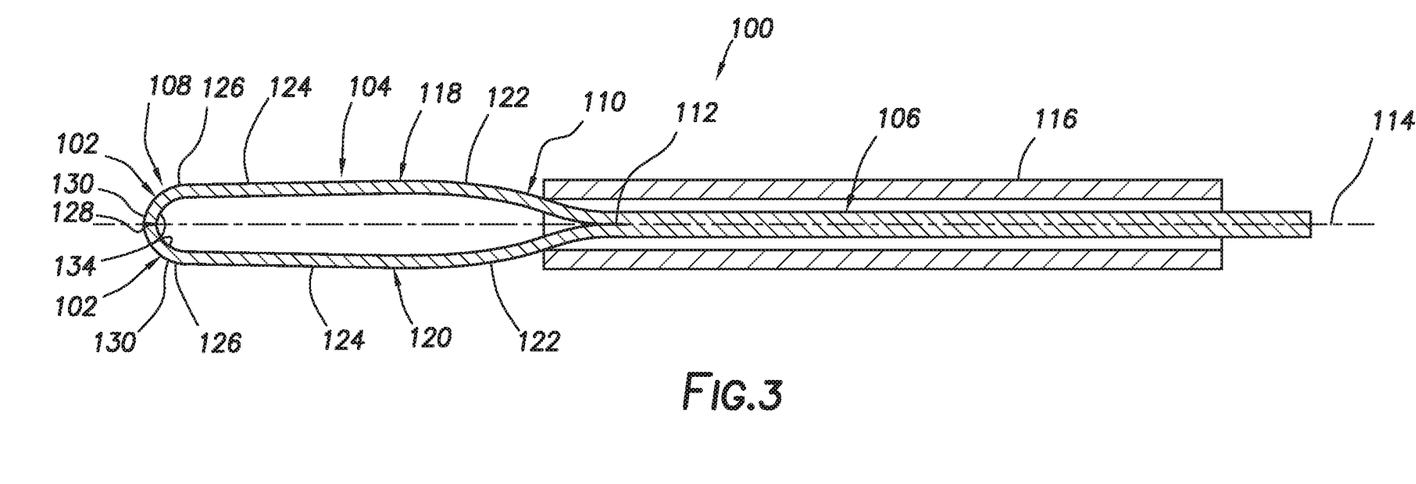
FIG. 3 illustrates a cross-sectional view of an example membrane forceps in a closed configuration.

With reference now to FIGS. 1 and 3, closing of the membrane forceps 100 will now be described in accordance with an example embodiment. FIG. 1 illustrates the membrane forceps 100 in an open configuration. FIG. 3 illustrates the membrane forceps 100 in a closed configuration. To close the membrane forceps 100, at least one of the actuation tube 116 and the forceps jaws 14 may be moved longitudinally relative to each other. For example, the actuation tube 116 may be slid at least partially over the forceps jaws 104 by being moved distally toward the distal end 108. As the actuation tube 116 moves toward the distal end 108, the actuation tube 116 engages the proximal ends 110 of the first jaw 118 and the second jaw 120 compressing together the first jaw 118 and the second jaw 120. Compression of the first jaw 118 and the second jaw 120 also moves the gripping tips 128 together. The actuation tube 116 may be positioned (as shown in FIG. 3) onto the forceps jaws 104 such that the gripping tips 128 abut one another so that a material (e.g., membrane 1010 shown in FIGS. 10-12 and 14) may be grasped between the gripping tips 128.

Figure 4:
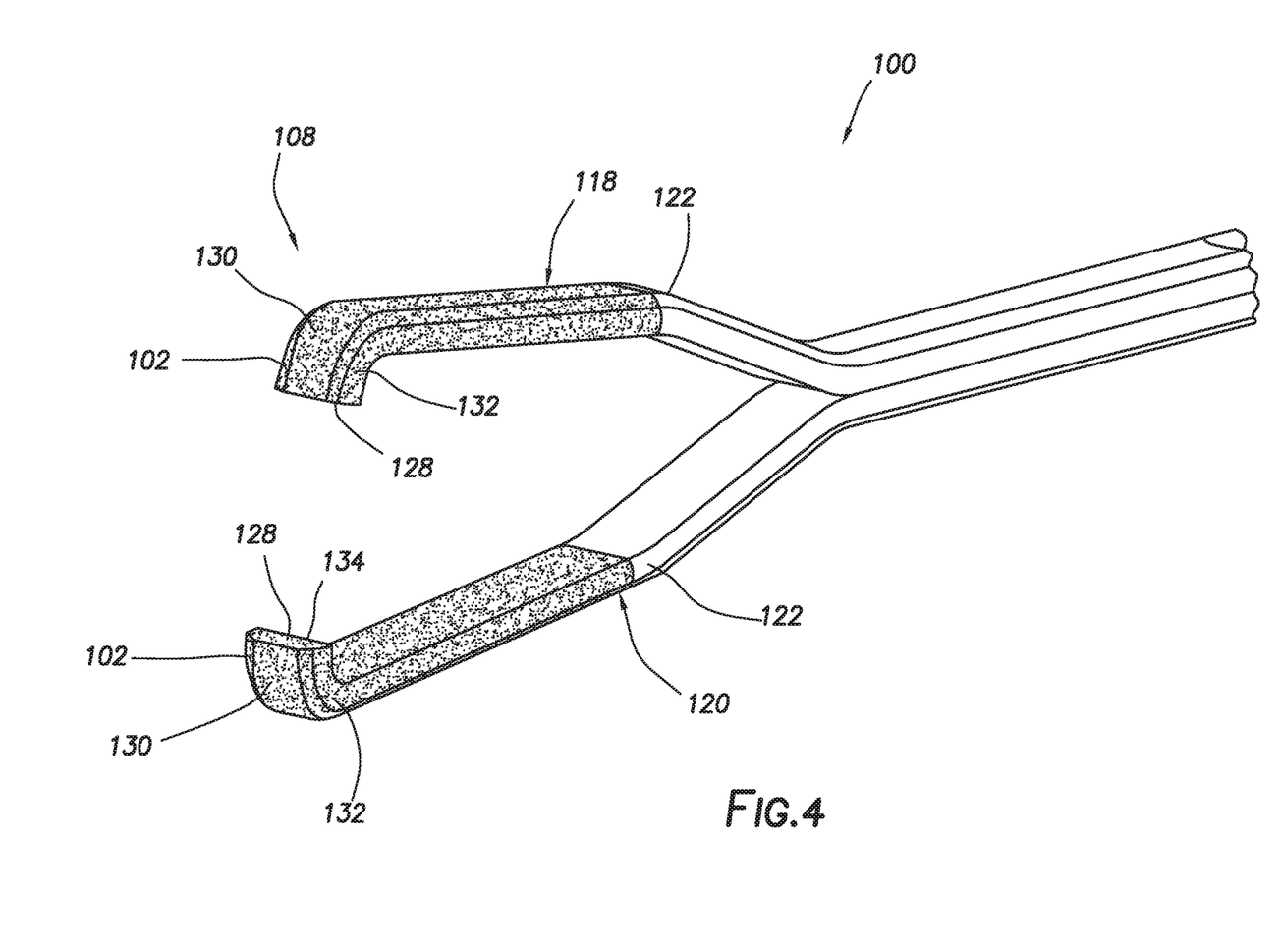
FIG. 4 illustrates a perspective view of another example membrane forceps in an open configuration.

FIG. 4 illustrates another example of the membrane forceps 100 with the coating 102. In the illustrated embodiment, the coating 102 completely covers the distal end 108 of the membrane forceps 100. As shown and according to some embodiments, the coating 102 also extends along the middle portions 124 of the first jaw 118 and the second jaw 120. In the illustrated example of FIG. 4, the coating 102 extends to the first bend 122. As shown in FIG. 4, the coating 102 covers the entire leading surface 130 of the first jaw 118 and the second jaw 120. In addition to the leading surface 130, the coating 102 may also cover the gripping tip 128, lateral surfaces 132, and trailing surface 134 of the first jaw 118 and the second jaw 120. An amount of the first and second jaws 118 and 120 covered by the coating 102 may depend, for example, on the coating technique used to apply the coating 102. However, the extent to which the first and second jaws 118 and 120 are coated with the coating 102 may be selected based on any desired criteria or no criteria. That is, an amount by which the first and second jaws 118 and 120 are coated may be unrelated to the use of the membrane forceps 100 or the coating technique used to apply the coating 102.

Any of a variety of materials may be used for the coating 102 that can increase the coefficient of friction. The coating 102 should have a coefficient of friction that is greater than a coefficient of friction of the leading surface 130 when uncoated. For example, the coating 102 may have a coefficient of friction that is about 5%, 10%, 20%, 30%, 40%, 50%, or more than a coefficient of friction of the uncoated leading surface 130. By having an increased coefficient of friction as compared to the leading surface 130 without the coating 102, desirable friction forces may be obtained between the membrane forceps 100 and a material (e.g., membrane 1010 shown in FIGS. 10-12 and 14), resulting in a reduced normal force needed to successfully grasp the material. As a result, indentation into the material may be reduced.

Example coatings 102 within the scope of the disclosure may be electrically charged (e.g., positively charge or negatively charge) or non-charged. Use of the coatings 102 with a charge may increase the coefficient of friction due to the electrical charge. Examples of suitable coatings 102 with an electric charge may include, but are not limited to: a positively charged, hydrophilic amine coating; a negatively charged, sulfonate coating; a multilayer polyelectrolyte coating; and a negatively charged hydroxyl coating. In some embodiments, the amine coating may include a polymer substrate having an amine incorporated into the polymer substrate, also referred to as an "amine-rich" coating. In some embodiments, the sulfonate coating may include a polymer substrate having a sulfonate incorporated into the polymer substrate, also referred to as a "sulfonate-rich" coating. In some embodiments, the multilayer polyelectrolyte coating may include alternating positive and negative polyelectrolyte layers. In some embodiments, the hydroxyl coating may include a polymer substrate having hydroxyl groups incorporated into the polymer substrate, also referred to as a "hydroxyl-rich" coating. Additional examples of the coating 102 may include a non-charged polydimethyl siloxane coating. The non-charged polydimethyl siloxane coating may have a softness that aligns with the material (e.g., membrane 1010 shown in FIGS. 10-12 and 14) to increase the coefficient of friction and, thus, friction forces. Additional examples of the coating 102 may be textured, such as a pillar coating or a suction-cup coating. In some embodiments, the coating 102 may be textured to have a defined surface structure and flexible behavior. For example, a coating of pillars (also referred to a pillar coating) may include application of pillars to the leading surface 130, and a coating of suction cups (also referred to as suction-cup coating) may include application of suction cups to the leading surface 130.

Figure 5:
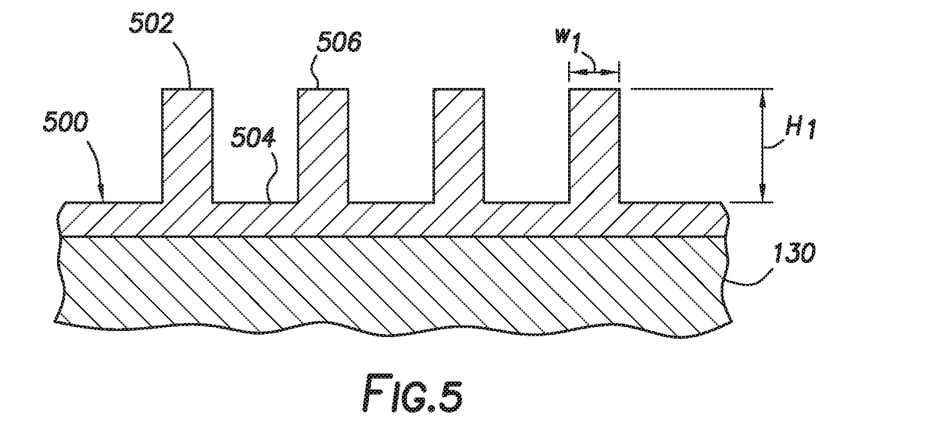
FIG. 5 is a side view of a membrane engagement surface of an example membrane forceps.

FIG. 5 illustrates an example pillar coating 500 disposed on the leading surface 130. As illustrated, the pillar coating 500 may include pillars 502 arranged on the leading surface 130. By increasing the contact area, the pillars 502 are believed to increase the coefficient of friction and resultant friction force. The pillars 502 may have cylindrical shapes or non-cylindrical shapes. The pillars 502 may have a height $H_1$ extending from a base or trough 504 of the pillar coating 500 to a peak 506. The height $H_1$ may range from 10 to 200 microns and a width $W_1$ ranging from about 1 micron to about 100 microns (e.g., about 10 microns to about 30 microns). In some implementations, the width $W_1$ may be a diameter of the pillars where the pillars are cylinders having circular cross-sections. However, dimensions $H_1$ and $W_1$ for the pillars 502 outside these ranges are also contemplated.

Figure 6:
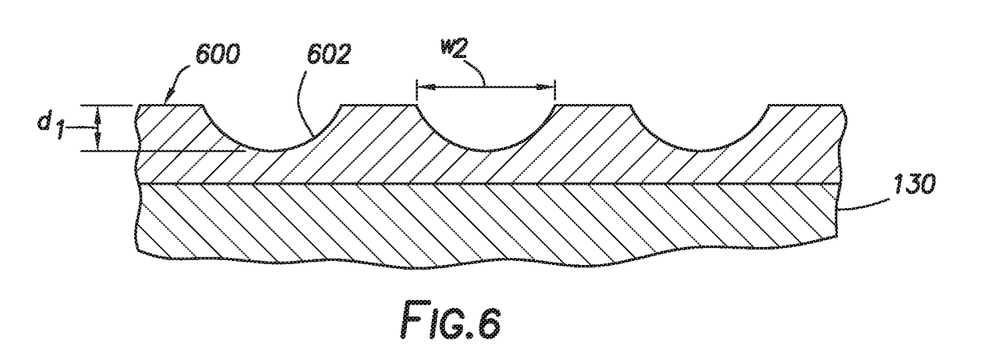
FIG. 6 is a side view of a membrane engagement surface of another example membrane forceps.
Figure 7:
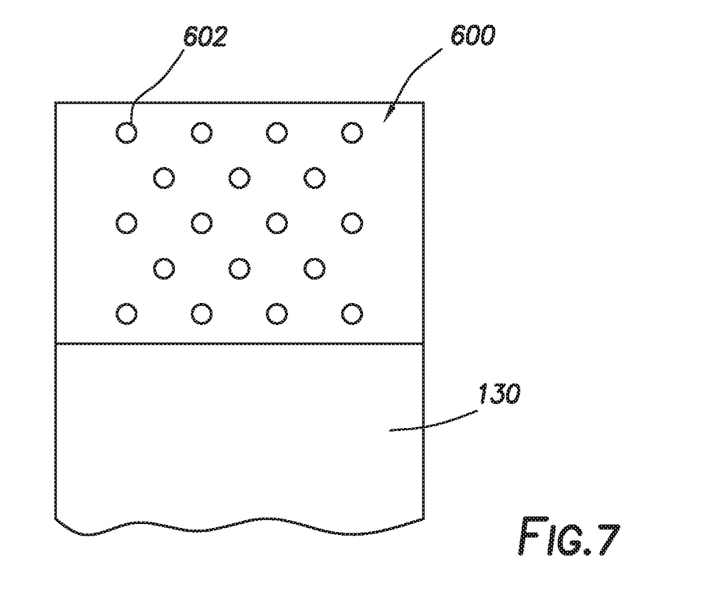
FIG. 7 is a top view of the membrane engagement surface of FIG. 6.

FIGS. 6 and 7 illustrate an example suction-cup coating 600 arranged on the leading surface 130. Recesses 602 may be formed in the suction-cup coating 600. The recesses 602 may act as suction cups, sticking when pressed against a material (e.g., membrane 1010 shown in FIGS. 10-12 and 14). By including a number of the recesses 602, the adhesive force of the suction-cup coating 600 may be increased. The recesses 602 may be spaced in the suction-cup coating 600 in any desired arrangement, including a spacing between the recesses 602 of about 5 microns to about 100 microns. However, additional or fewer recesses 602 are contemplated. Further, the number of recesses 602 included may depending on one or more factors including, for example, an application for which the membrane forceps 100 is to be employed and/or a configuration of the recesses 602. The recesses 602 may be circular, square, or rectangular in shape. The recesses 602 may also form other types of shapes. The recesses 602 may have a depth $d_1$ ranging from 1 micron to about 100 microns and a width $W_2$ (which may define a diameter in the instances where the recesses 602 are in the form of a circle) ranging from about 1 micron to about 100 microns (e.g., about 10 microns to about 30 microns). However, dimensions of depth $d_1$ and width $W_2$ of the recesses 602 outside these ranges are also contemplated.

Figure 8:
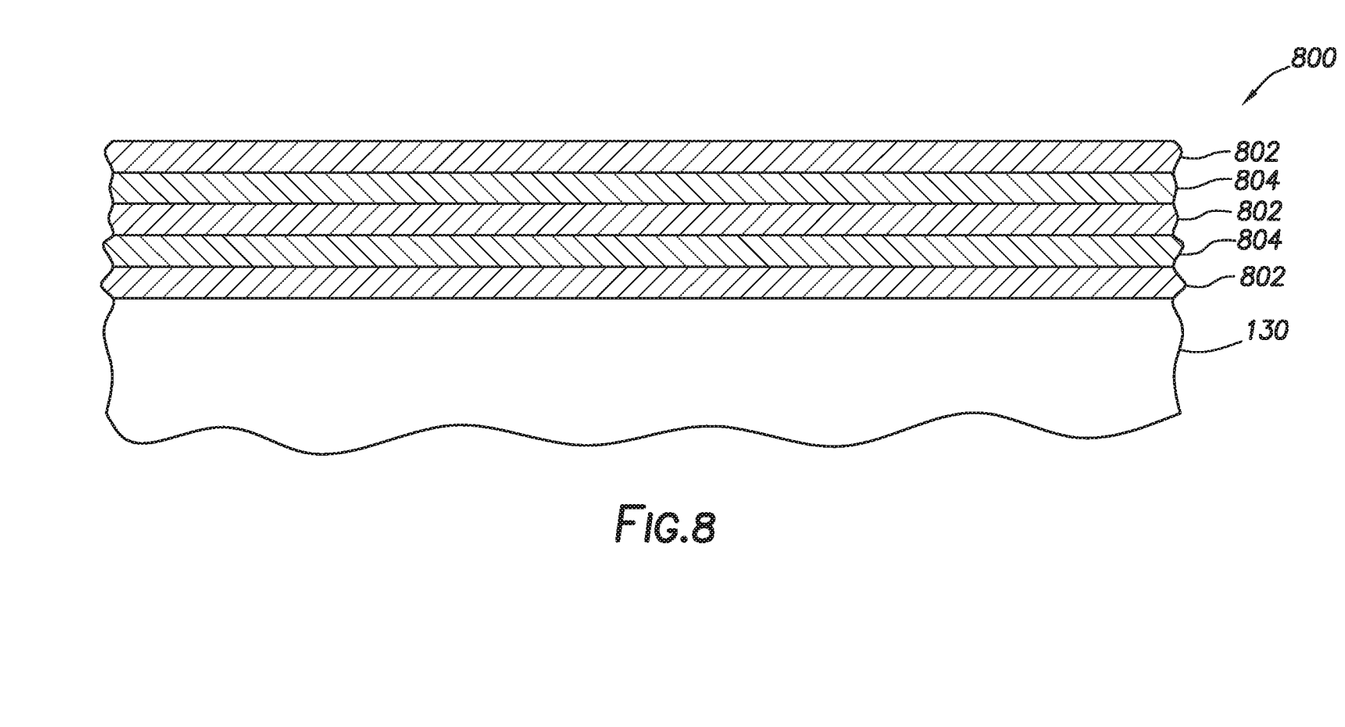
FIG. 8 is a side view of a membrane engagement surface of another example membrane forceps.

FIG. 8 illustrates an example multilayer polyelectrolyte coating 800 arranged on the leading surface 130. As illustrated, the multilayer polyelectrolyte coating 800 may include positively charged layers 802 and negatively charged layers 804. The positively charged layers 802 may alternate with the negatively charged layers 804. While three of the positively charged layers 802 and two of the negatively charged layers 804 are shown, more or less of the positively charged layers 802 and/or the negatively charged layers 804 may be used in accordance with example embodiments.

Figure 9:
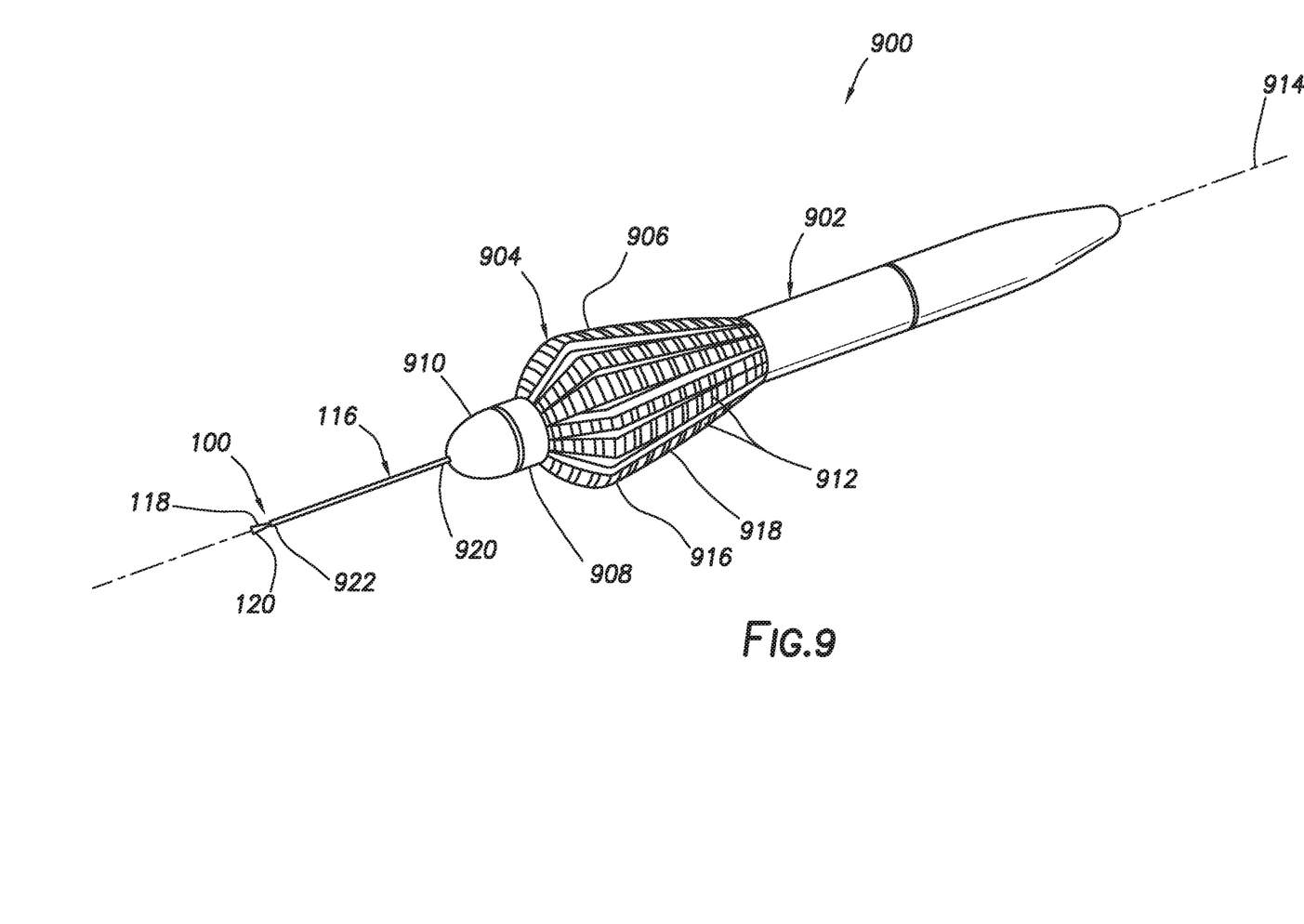
FIG. 9 is a perspective view of a surgical instrument that includes an example membrane forceps.

FIG. 9 illustrates an example surgical instrument 900 that includes the membrane forceps 100. In the illustrated embodiment, the surgical instrument 900 may include a handle 902, a tube actuation assembly 904, the actuation tube 116, and the membrane forceps 100. The handle 902 may have any suitable shape, including cylindrical as shown, to an enable a surgeon to manipulate the membrane forceps 100 into a desired positon. The handle 902 may be made from any suitable material, including, but not limited, to a metal or thermoplastic, among others. While not illustrated, the handle 902 may include texturing or knurling to improve gripping.

The tube actuation assembly 904 may be disposed between the handle 902 and the actuation tube 116. The tube actuation assembly 904 may include an actuator portion 906, a sleeve 908, and a nose cone 910. In some embodiments, the actuator portion 906 may include longitudinal extensions 912. The longitudinal extensions 912 may extend over a portion (not shown) of the sleeve 908 and may be arranged around longitudinal axis 914 of the surgical instrument 900. The longitudinal extensions 912 may each include a bend 916 so that the longitudinal extensions 912 may be arcuate in shape with a central portion 918 that extends away from the longitudinal axis 914. The longitudinal extensions 912 may be made from any suitable material with elasticity so that the longitudinal extensions 912 may resume their normal shape (e.g., arcuate shape) after squeezing of the actuator portion 906 radially. Suitable materials may include, but are not limited to, titanium, stainless steel, polymers, e.g., thermoplastics, or shape-memory metals, among others. The longitudinal extensions 912 may be formed so that squeezing of the actuator portion 906 causes the longitudinal extensions 912 to extend along the longitudinal axis 214, for example, by straightening of the bend 916. The longitudinal extensions 912 may be coupled to the sleeve 908. The sleeve 908 and the nose cone 910 may be coupled to one another so that extension of the length of the longitudinal extensions 912 should cause the sleeve 908 and the nose cone 910 to move longitudinally. The sleeve 908 and the nose cone 910 may be made from any suitable material, including, but not limited, to a metal or polymer, e.g., a thermoplastic, among others.

The actuation tube 116 may be coupled to the nose cone 910. In some embodiments, the actuation tube 116 may be a hollow tube. The actuation tube 116 may include a proximal end 920 and a distal end 922. The proximal end 920 of the actuation tube 116 may be coupled to the nose cone 910 so that movement of the nose cone 910 may be transferred to the actuation tube 116. The actuation tube 116 may be made from any suitable material, including, but not limited to, a metal or polymer, e.g., a thermoplastic, among others.

The membrane forceps 100 may extend from the distal end 922 of the actuation tube 116. Any of a variety of techniques may be used for operation of membrane forceps 100, including use of tube actuation assembly 904. In operation, the tube actuation assembly 904 may be operated to cause the membrane forceps 100 to close. For example, squeezing of the actuator portion 906 may force the sleeve 908 and the nose cone 910 forward relative to the handle 902. The forward movement of the sleeve 908 and the nose cone 910 may be transferred to the actuation tube 116, causing the distal end 922 of the actuation tube 116 to slide partially over the membrane forceps 100, causing the membrane forceps 100 to close, as described above with respect to FIGS. 1 and 3. The amount of movement of the actuation tube 116 over the membrane forceps 100 may be controlled, for example, by varying the outer diameter of the actuator portion 906 in its relaxed state. It should be understood that the tube actuation assembly 904 has been described as an illustrative example for actuation of the membrane forceps 100 and embodiments of the present disclosure may be used with other techniques for closing the membrane forceps 100.

Figure 10:
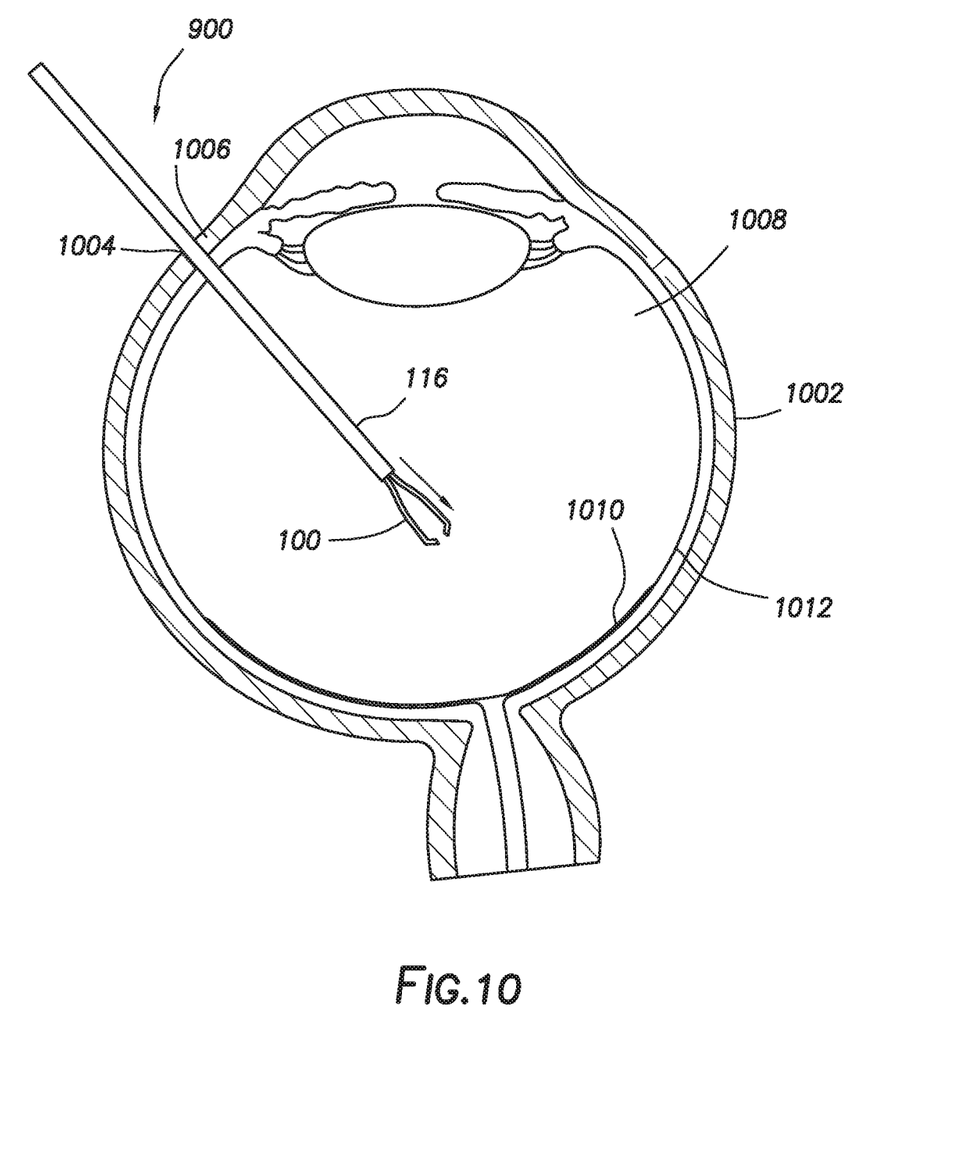
FIG. 10 illustrates membrane forceps disposed within an eye of a patient in an example vitreoretinal procedure.
Figure 11:
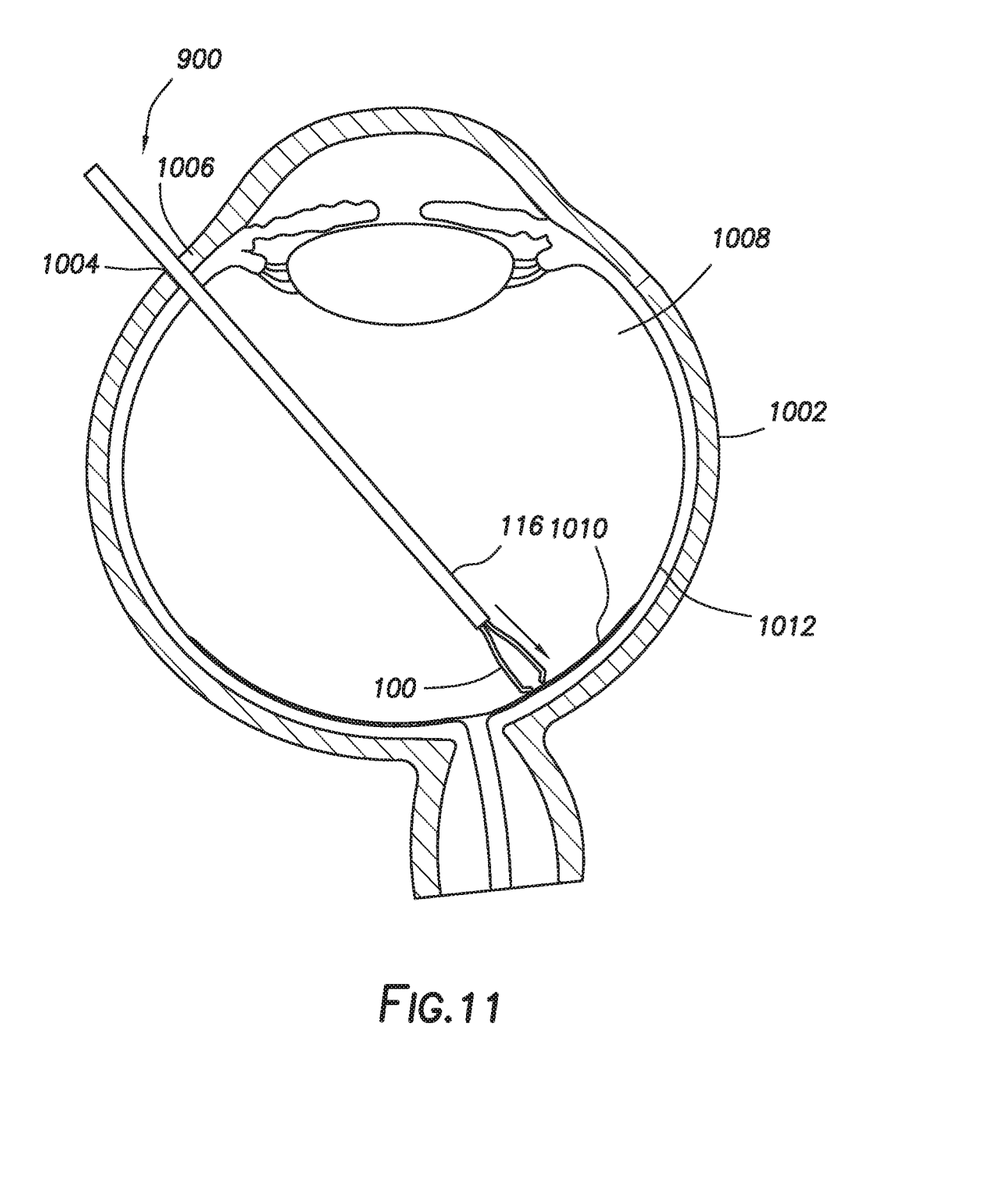
FIG. 11 illustrates membrane forceps disposed within an eye of a patient in an example vitreoretinal procedure.
Figure 12:
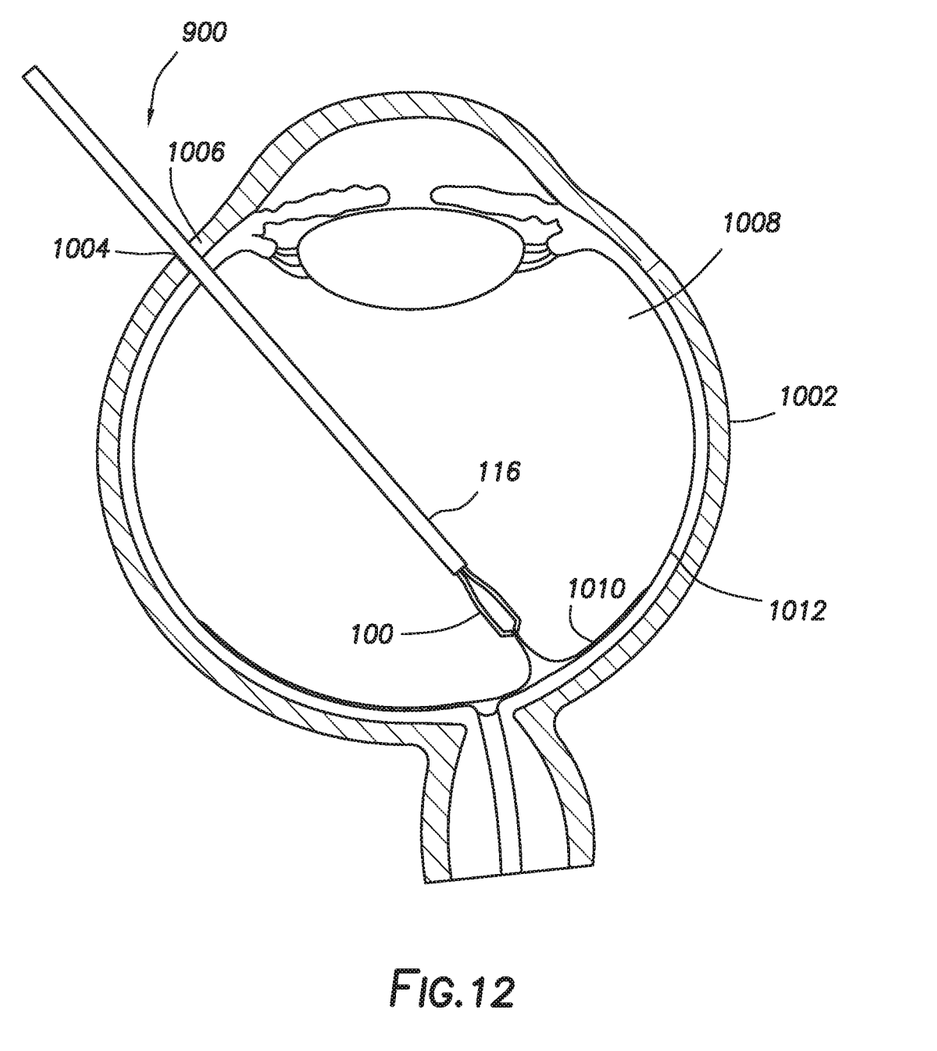
FIG. 12 illustrates membrane forceps disposed within an eye of a patient in an example vitreoretinal procedure.

FIGS. 10-12 illustrate an example technique that uses the membrane forceps 100 in a surgical procedure. In FIG. 10, a surgical instrument 900 may be inserted into an eye 1002 of a patient. In the illustrated embodiment, the surgical instrument 900 may be inserted through an incision 1004 in the friction sclera 1006. While not shown, additional instruments, such as an illuminator to provide illumination, may also be inserted into the eye 1002. The surgical instrument 900 may be advanced through the interior 1008 of the eye 1002 to a membrane 1010 on a retina 1012. For example, the membrane 1010 may be an inner limiting membrane. With reference now to FIG. 11, the surgical instrument 900 may be moved such that the membrane forceps 100 are in contact with the membrane 1010. As illustrated on FIG. 12, the membrane forceps 100 may then be closed to grasp and peel the membrane 1010 away from the retina 1012. The actuator tubing 116 may be slid down onto the membrane forceps 100 to close the membrane forceps 100 onto the membrane 1010. Due to the increased coefficient of friction between the membrane forceps 100 and the membrane 1010 caused by the coating 102 (e.g., shown on FIG. 1), there is sufficient friction force for the membrane forceps 100 to grasp the membrane 1010 as the membrane forceps 100 are being closed, peeling the membrane from the retina 1012.

Figure 13:
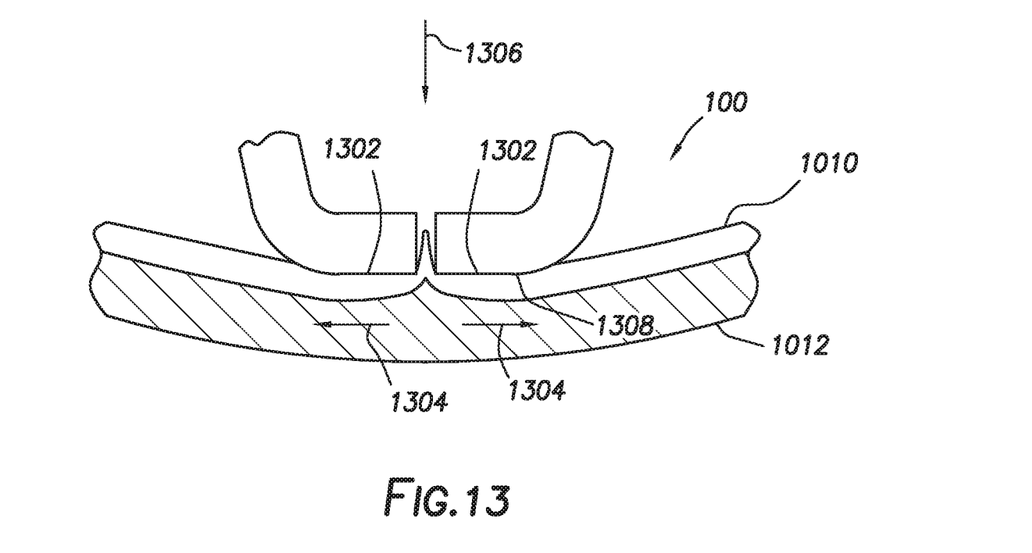
FIG. 13 illustrates use of uncoated membrane forceps grasping a membrane in an example vitreoretinal procedure.

FIG. 13 illustrates conventional membrane forceps 1300 where a leading surface 1302 is not coated. The membrane forceps 1300 is shown grasping a membrane 1010, which is disposed on retina 1012. A friction force 1304, indicated on FIG. 13 by horizontal arrows, is needed for the leading surface 1302 of the membrane forceps 1300 to grip the membrane 1010. The membrane forceps 1300 also apply a normal force 1306, indicated on FIG. 13 by a vertical arrow, to the membrane 1010. The friction force 1304 is equal to the coefficient of friction times the normal force 1306. To generate the friction force 1304 sufficient for grasping the membrane 1010, the normal force 1306 typically generates an indentation 1308 in the membrane 1010 and the retina 1012 underlying the membrane. This normal force 1306 and indentation 1308 can damage the retina 1012.

Figure 14:
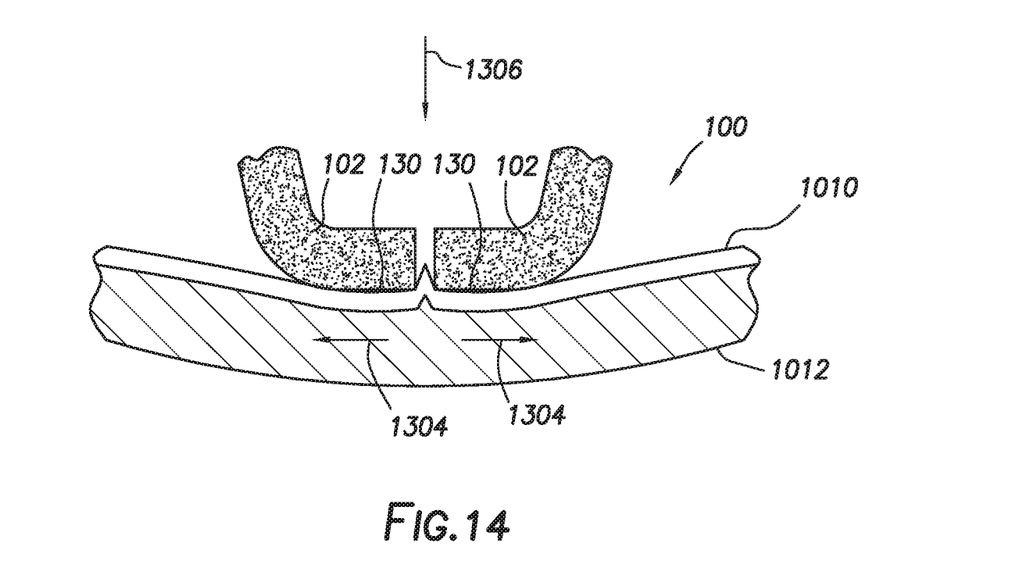
FIG. 14 illustrates use of membrane forceps that are coated and grasping a membrane in an example vitreoretinal procedure.

FIG. 14 illustrates use of the membrane forceps 100 with the coating 102 on the leading surface 130. The membrane forceps 100 is shown grasping a membrane 1010, which is disposed on retina 1012. Because the coating 102 increases the coefficient of friction, the friction force 1304 can be sufficient to grasp the 1010 with the normal force 1306 being reduced. As a result, damage to the retina 1012 from peeling the membrane 1010 may be reduced and potentially even eliminated.

It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

What is claimed is:

1. A membrane forceps, comprising:
   a forceps extension; and
   forceps jaws extending from a distal termination of the forceps extension, the forceps jaws comprising:
   a first jaw comprising a first gripping tip;
   a second jaw, comprising a second gripping tip; and
   a coating disposed on a distal end of the forceps jaws, the coating configured to increase a coefficient of friction with a membrane, the first gripping tip and the second gripping tip abutting one another when the forceps jaws are in a closed configuration;
   wherein the coating comprises a charged coating;
   wherein the charged coating comprises at least one coating selected from the group consisting of a positively charged, hydrophilic amine coating; a negatively charged, sulfonate coating; a multilayer polyelectrolyte coating; and a negatively charged hydroxyl coating.

2. The membrane forceps of claim 1, wherein the coating is disposed on at least a portion of a leading surface of each of the first jaw and the second jaw, the leading surface not including the gripping tips.

3. The membrane forceps of claim 1, wherein the coating comprises a textured coating.

4. The membrane forceps of claim 3, wherein the textured coating comprises a pillar coating or a suction-cup coating.

5. The membrane forceps of claim 1, wherein a surface of the forceps jaws covered by the coating excludes the first gripping tip and the second gripping tip.

6. The membrane forceps of claim 1, wherein the coating is disposed on a leading surface of each of the first jaw and the second jaw, the leading surface terminating at the corresponding first gripping tip and second gripping tip.

7. The membrane forceps of claim 6, wherein the first jaw and the second jaw are arcuate in shape, wherein the first jaw and the second jaw each comprise a first bend and a second bend, and wherein the second bend in each of the first jaw and the second jaw causes the distal end of the membrane forceps to curve toward a longitudinal axis of the membrane forceps.

8. The membrane forceps of claim 7, wherein the leading surface of each of the first jaw and the second jaw extends from the second bend to the corresponding gripping tip.

9. A membrane forceps, comprising:
   a forceps extension; and
   forceps jaws extending from a distal termination of the forceps extension, the forceps jaws comprising:
   a first jaw comprising a first gripping tip;
   a second jaw, comprising a second gripping tip; and
   a coating disposed on a distal end of the forceps jaws, the coating configured to increase a coefficient of friction with a membrane, the first gripping tip and the second gripping tip abutting one another when the forceps jaws are in a closed configuration;
   wherein the coating comprises a polydimethyl siloxane coating.

10. A surgical instrument, comprising:
    membrane forceps comprising:
    a forceps extension; and
    forceps jaws extending from a distal termination of the forceps extension, the forceps jaws comprising:
    a first jaw comprising a first gripping tip; and
    a second jaw comprising a second gripping tip;
    a coating formed on a distal end of each of the first jaw and the second jaw, the coating configured to increase a coefficient of friction with a membrane, the first gripping tip and the second gripping tip configured to abut one another when the forceps jaws are in a closed configuration; and
    an actuation tube, the forceps extension extending through the actuation tube;
    wherein the coating comprises a charged coating selected from the group consisting of: a positively charged, hydrophilic amine coating; a negatively charged, sulfonate coating; a multilayer polyelectrolyte coating; a negatively charged hydroxyl coating; and combinations thereof.

11. The surgical instrument of claim 10, wherein the coating is disposed on at least a portion of a leading surface of each of the first jaw and the second jaw, the leading surface not including the gripping tips.

12. The surgical instrument of claim 10, wherein the coating comprises a polydimethyl siloxane coating.

13. The surgical instrument of claim 10, wherein the coating comprises a textured coating selected from the group consisting of a pillar coating, a suction-cup coating, and combinations thereof.

14. The surgical instrument of claim 10, wherein a surface of the forceps jaws covered by the coating excludes the first gripping tip and the second gripping tip.

15. The surgical instrument of claim 10, wherein surgical instrument further comprises:
    a handle; and
    a tube actuation assembly coupled to the handle and the actuation tube, wherein the tube actuation assembly is operable to close the forceps jaws by causing the actuation tube to move over the forceps jaws.

* * * * *